United States Patent [19]

Stevens

[11] 4,000,739
[45] Jan. 4, 1977

[54] HEMOSTASIS CANNULA
[75] Inventor: Robert C. Stevens, Miami, Fla.
[73] Assignee: Cordis Corporation, Miami, Fla.
[22] Filed: July 9, 1975
[21] Appl. No.: 594,521
[52] U.S. Cl. .............................. 128/214.4; 128/2 A
[51] Int. Cl.² ......................................... A61M 5/00
[58] Field of Search .............. 128/214.4, 221, 272, 128/2 F, 2 A

[56] References Cited
UNITED STATES PATENTS

| | | | |
|---|---|---|---|
| 2,022,369 | 11/1935 | Curtis | 128/272 |
| 3,459,183 | 8/1969 | Ring et al. | 128/214.4 |
| 3,585,996 | 6/1971 | Reynolds | 128/214.4 |
| 3,659,587 | 5/1972 | Baldwin | 128/2 F |
| 3,825,001 | 7/1974 | Bennet et al. | 128/214.4 |

FOREIGN PATENTS OR APPLICATIONS
430,890  10/1911  France ................. 128/221

Primary Examiner—Dalton L. Truluck
Attorney, Agent, or Firm—Kenway & Jenney

[57] ABSTRACT

Hemostasis cannula comprising a body having a passage therethrough adapted to receive a catheter and a pair of juxtaposed gaskets mounted in the passage. The first gasket forms a seal around a catheter enclosed within the cannula; the second gasket is compressed against the first to seal the passage when the catheter is removed. The cannula also features a flexible entrance tube and a port for introducing fluids into a patient's blood vessel.

4 Claims, 4 Drawing Figures

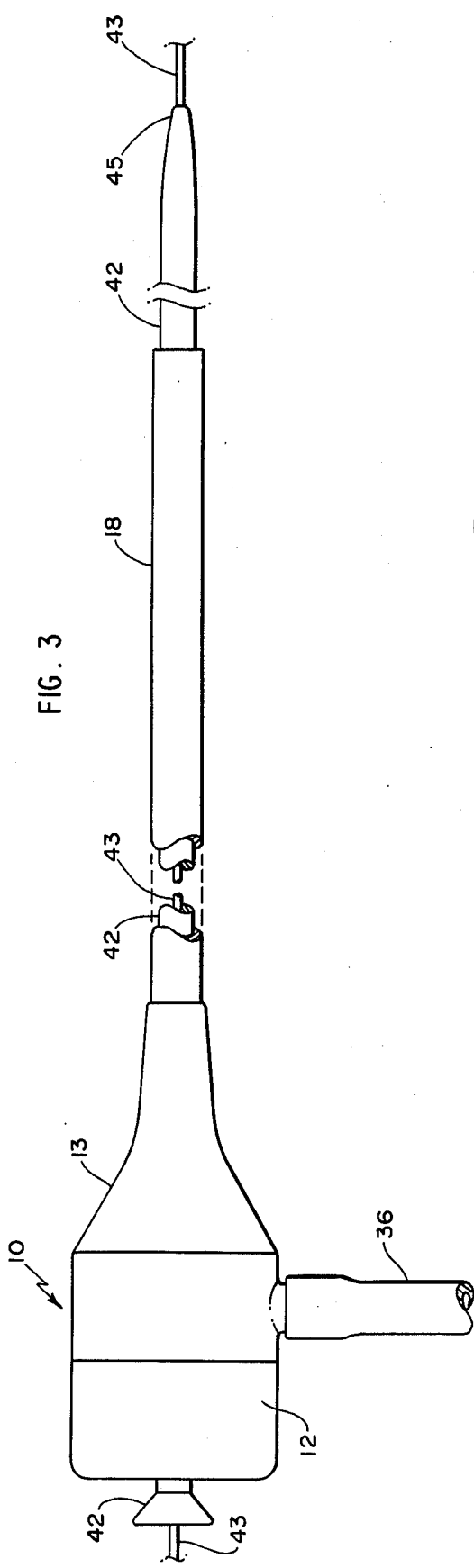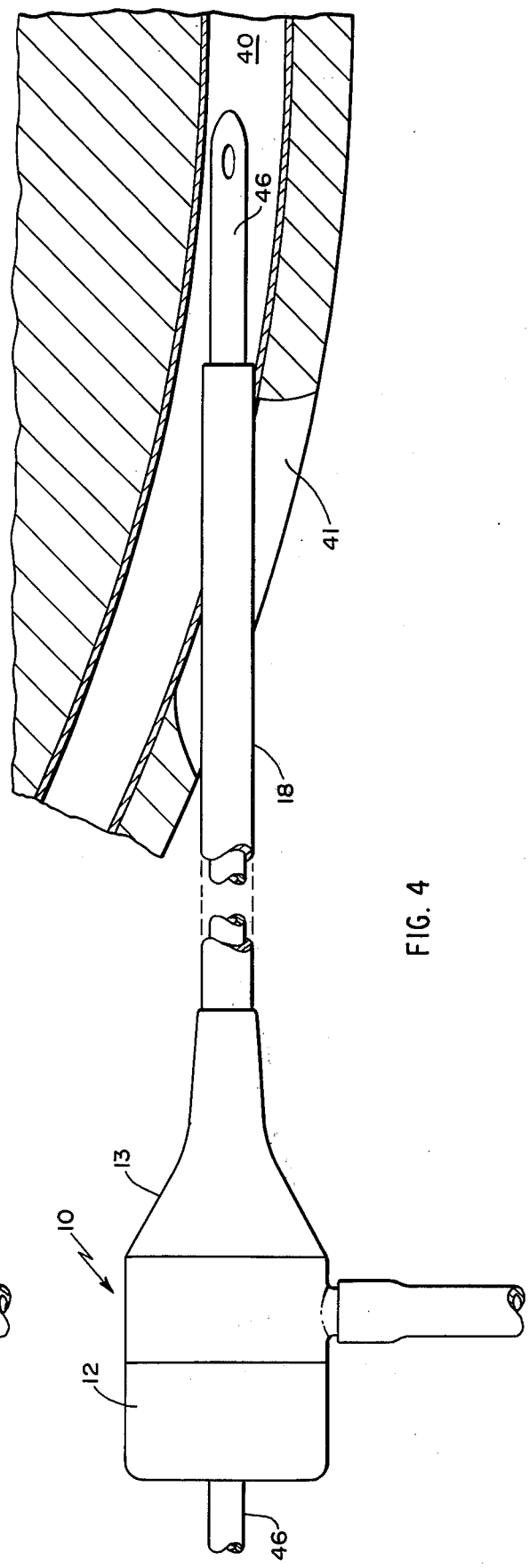

HEMOSTASIS CANNULA

BACKGROUND OF THE INVENTION

This invention relates to cannulas, especially those used for positioning and manipulating intravascular catheters known as angiographic catheters.

Angiography is a well-known and very valuable procedure used to diagnose vascular and organ disease. It involves the introduction of a hollow tubular catheter into one of the major arteries or veins, such as the femoral or brachial arteries, and advancing and maneuvering it into smaller branching vessels which are to be studied. After the catheter is in position, a radio-opaque fluid is injected through the catheter into the vascular system to be studied and an x-ray picture is taken of the now x-ray opaque vascular structure.

Prior art techniques for introducing such catheters include what is known as the "cut down" method and various modifications of the "Seldinger" technique. The "cut down" technique involves surgically opening a vein or artery and introducing the angiographic catheter directly through the incision. This method inevitably involves the loss of blood through the incision as well as venous ligation and arterial repair. The use of this method renders it particularly difficult to employ the same vessel when multiple studies are indicated.

*The American Journal of Cardiology*, Vol. 30, Sept., 1972, at page 378, describes an alternative method of cardiac catheterization, a modification of the Seldinger technique, wherein a percutaneous sheath is introduced into the lumen of a blood vessel. A hollow needle is inserted through the skin and into the lumen; a guide wire is passed through the needle and advanced up the artery or vein into the organ to be studied; the needle is removed, leaving the guide wire in the vessel; a sheath and dilator unit are advanced over the wire into the vessel, and; the dilator is removed along with the guide wire. Now, any type of catheter desired of similar diameter, can be inserted through the sheath into the vessel. To avoid excessive bleeding, and to ensure against the possibility of an air embolism, this technique requires the physician to occlude the orifice of the sheath during catheter changes. The procedure suffers from the possibility of a blood clot migrating to the heart, lungs, or extremities. Blood loss through the annular space between the sheath and the catheter is difficult to avoid.

Both these methods are also characterized, especially if multiple studies are indicated, by venous thrombosis, subcutaneous hematomas, and other considerable discomfort to the patient. Obviously, neither of these methods is totally satisfactory.

SUMMARY OF THE INVENTION

It is therefore an object of this invention to provide a cannula which can be left in the vessel during angiographic or other catherterization while the catheter is manipulated within the cannula and vessel. When the catheter is in place there is no blood loss, yet restriction of catheter manipulation is minimized. A seal capable of withstanding a minimum blood pressure of 300 mm, when the catheter has been removed, is also provided, thus obviating the necessity of occluding the cannula and preventing significant blood loss at all times. Another object of the invention is to provide a cannula having a minimum area of stagnation within the cannula body portion. Still another object of the invention is to provide means by which the cannula body and tubing can be flushed at all times to prevent clotting within the cannula or at the interface of the cannula and catheter. Catheter insertion is simply accomplished by the use of a disposable guide and dilator unit. A flexible tube provides communication through the wall of the artery, hence reducing the danger of unwanted puncturing of the wall. It also eliminates the possibility, such as that present when a sharp hollow needle is used as a cannula, of cutting off pieces of catheter during its withdrawal.

In general, the invention features a hemostasis cannula comprising a body having a passage therethrough adapted to receive a catheter and having a pair of juxtaposed gaskets mounted in the passage in contact with each other. One of the gaskets has a round hole, the other a Y-shaped slit. The first gasket maintains a sealing relationship with the catheter and, upon withdrawal of the catheter from the passage, the gaskets cooperate to close the passage, since the gasket with the slit is compressed against the first gasket. In preferred embodiments, the cannula further includes a length of flexible tubing in fluid tight engagement with the body. A port communicating with the body of the cannula for introducing fluids into the patient's artery is also provided.

Other advantages and features will be apparent to those skilled in the art from the following description of a preferred embodiment of the invention and from the drawings wherein:

FIG. 3 is a view in side elevation of the cannula enclosing a dilator unit and guide;

FIG. 4 shows the embodiment of FIG. 1 in position in the lumen of a blood vessel with a catheter enclosed therein.

DESCRIPTION OF A PREFERRED EMBODIMENT

Figure 1:
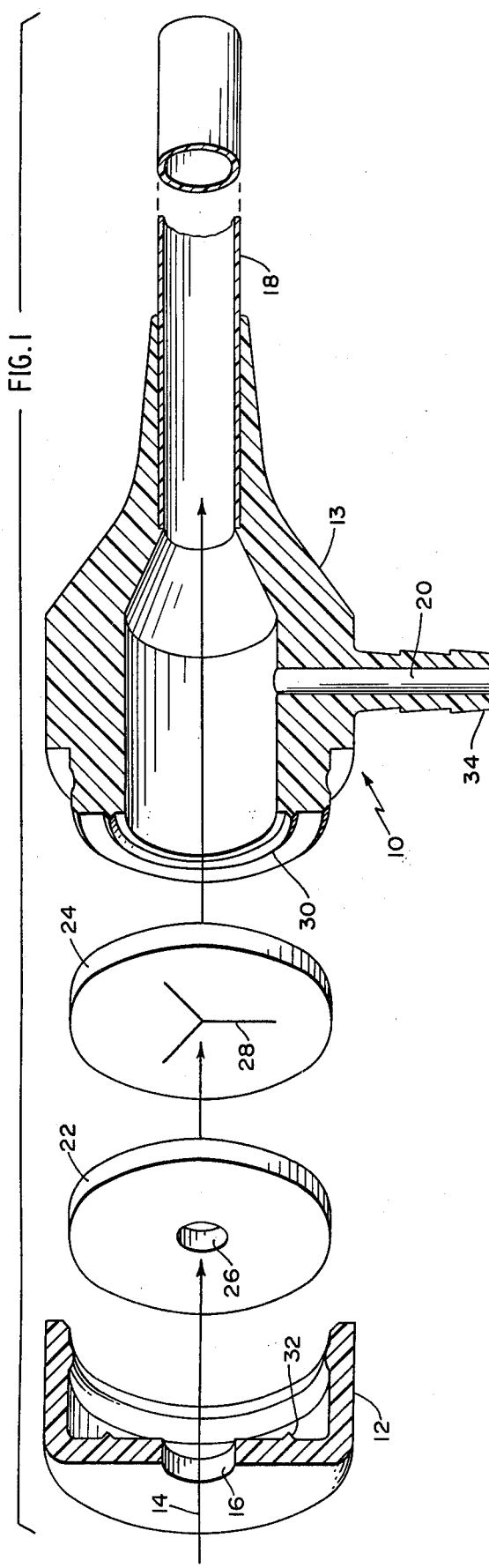
FIG. 1 is an exploded, partially cut-away view of an embodiment of the invention.
Figure 2:
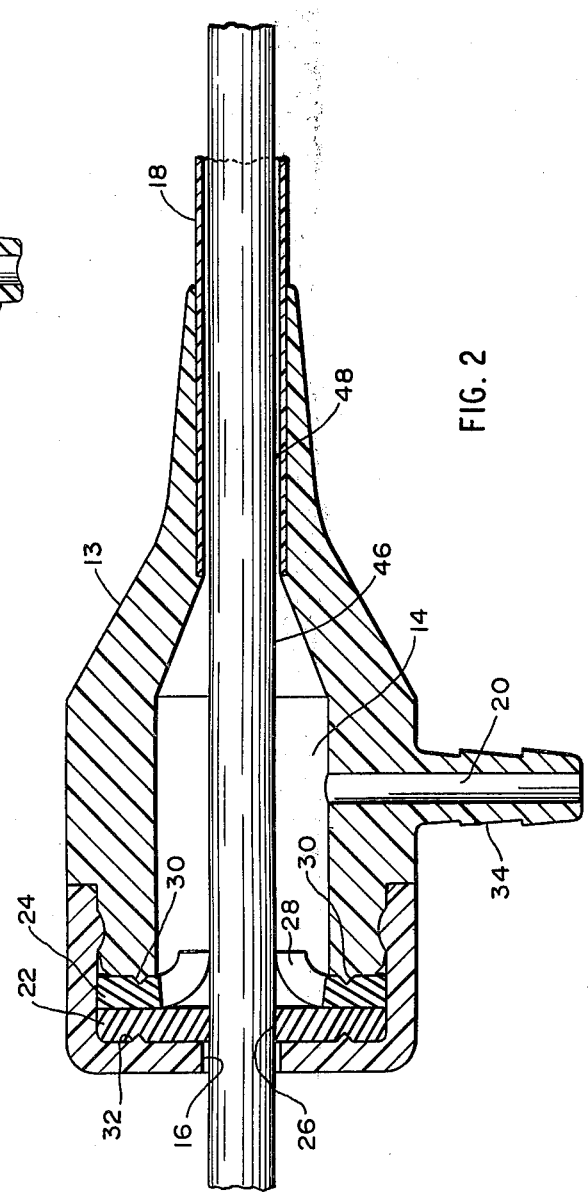
FIG. 2 is a view in cross-section of the embodiment of FIG. 1 with a catheter enclosed in the cannula.

As seen in FIG. 1, the cannula comprises a generally cylindrical hub or body portion 10 having a snap-on cap 12 and a tapered portion 13 leading to a length of flexible tubing 18. Within the body 10, is a passage generally designated by arrow 14. The body portion 10 and the entrance tube 18 may be conveniently made of any one of a number of well-known suitable plastic materials, e.g., high density polyethylene. A pair of gaskets 22, 24 are enclosed within cap 12. The annular gasket 22 has a centrally positioned hole 26 and is made of latex, silicon rubber, or other suitable sealing material. The hole 26 has a diameter slightly less than that of catheter 46, used with the cannula, so that, when catheter 46 is inserted through the passage 14, the gasket 22 will sealingly engage it, as shown in FIG. 2. The self-sealing gasket 24 has a Y-slit 28 centrally disposed therein. The slit permits relatively unobstructed passage of the catheter 46 therethrough, yet, when catheter 46 is not in position within the cannula, the slit closes, rests against the gasket 22, and withstands a minimum of 300 mm blood pressure, thereby preventing any blood flow back through the passage 14. The cap 12 has a centrally located hole 16, positioned co-axially with the gaskets 22, 24, and an annular ridge 32 which seals the gasket 22 against the cap 12. A second annular ridge 30, disposed on body 10, likewise acts to seal the gasket 24.

Formed integrally with the body 10 is a boss 34 extending laterally outwardly from the body 10 and containing a passage 20 leading into the passage 14. The boss 34 is stepped on its exterior to provide means for connection to a plastic tube 36 (FIGS. 3 and 4). A liquid may be introduced through the tube 36 for flushing the interior of the cannula hub portion and cannula tubing, thus helping prevent clotting within the cannula or at the interface of the cannula and catheter in the patient's vessel.

So that blood will not flow through the flushing port 20, the physician will maintain positive pressure of flushing fluid throughout the operation.

As seen in FIG. 3, a hollow plastic dilator 42 having a diameter substantially equal to that of the catheter 46 may be positioned in passage 14 with its tapered end 45 extending beyond the distal end of the tube 18. After the cannula has been inserted in the vessel over guide 43, the dilator and guide may be removed and discarded.

In operation, an incision 41 is made in the patient's skin close to the vessel to be used, and a hemostat is introduced into the incision and maneuvered through the tissue until the vessel is exposed. A hollow needle into which a solid, sharp-ended trocar has been inserted (not shown) is then introduced into the vessel. When the lumen 40 of the vessel has been penetrated, the trocar is removed and replaced by a guide 43, then the needle is removed. The hollow plastic dilator 42 is now threaded through passage 14 of the cannula, as shown in FIG. 3, and slipped over the guide 43. The physician then dilates the hole through the vessel wall by maneuvering the tapered end 45 of the dilator 42 therethrough and introduces the entrance tube 18 into the vessel lumen 40. Now the cannula is taped in position on the body of the patient, and, with the feed tubing 36 fastened to the connector 34 and while maintaining a slow flow of heparin saline solution, the physician withdraws the dilator 42 and guide 43. At this point, the slit 28 in the gasket 24 closes and, with the support of adjacent gasket 22, resists the force exerted by the patient's blood pressure and prevents any blood loss. The catheter is now introduced through the hole 16 and passes through the gaskets 22 and 24; it is guided through hub 10 and into tube 18 by the tapered portion 13. It finally passes into the lumen 40 of the blood vessel (FIG. 4). As seen in FIG. 2, the slit 28 of the gasket 24 opens to allow passage of the catheter; the annular gasket 22 forms a seal around the exterior of the catheter 46, thereby preventing any blood loss through the entrance hole 16. The gasket 24 yields easily to the catheter and does not inhibit its manipulation. The annular space 48 (FIG. 2) between the catheter 46 and the entrance tube 18 is constantly flushed by a flow of heparin saline solution introduced through the port 20 and the tubing 36 to prevent clotting. When the catheter 46 has been maneuvered into position, radio-opaque fluid is injected therethrough, and an x-ray photograph is taken of the now radio-opaque vascular system of the organ being studied.

If multiple studies are indicated, or if the catheter has not been positioned correctly, it is a simple matter to remove the catheter and introduce another. A guide wire may be used if appropriate. Since, on removal of the cather 46, the gaskets 22 and 24 close together to reseal the entrance hole 16, no bleeding is experienced by the patient. If desired, with the catheter removed, other fluids, such as anesthetic or intravenous feeding solution, may be introduced into the vessel through tube 36. Either a closed or opened end catheter may be conveniently inserted through the cannula of the invention.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A hemostasis cannula comprising a body having a passage therethrough adapted to receive a catheter, a first disc-like gasket having a round hole disposed therein mounted in said passage, and a second disc-like gasket having a Y-slit located therein, said second gasket being mounted in said passage in face-to-face contact with said first gasket, said first gasket being operable to maintain a seal around and to allow manipulation of a catheter contained in said passage, the face-to-face relationship of said gaskets serving to support said second gasket in its closed position when a catheter is absent from said passage.

2. The cannula of claim 1 further comprising a length of flexible tubing in fluid-tight engagement with said body.

3. The cannula of claim 1 further comprising a port communicating with said passage for introducing fluids into a patient's blood vessel.

4. A hemostasis cannula comprising
   a body having a passage therethrough adapted to receive a catheter;
   first and second disc-like gaskets mounted in said passage in face-to-face contact, said first gasket having a hole disposed therein, and said second gasket having a slit therein;
   a length of flexible tubing in fluid-tight engagement with said body; and,
   a port communicating with said body for introducing fluids into a patient's blood vessel, said first gasket being operable to maintain a sealing relationship with a catheter contained in said passage and, when a catheter is not contained in said passage, said gaskets being operable to cooperate to close said passage, said second gasket being compressed against the first to close both the slit and the hole.

* * * * *